(12) United States Patent
Maggioni

(10) Patent No.: US 7,393,340 B2
(45) Date of Patent: Jul. 1, 2008

(54) DISPOSABLE SAFETY SYRINGE INCLUDING AN AUTOMATICALLY RETRACTABLE NEEDLE

(75) Inventor: Tarcisio Maggioni, Brugherio (IT)

(73) Assignee: Tecnedil S.r.l., Brugherio, Milan (IT)

( * ) Notice: Subject to any disclaimer, the term of this patent is extended or adjusted under 35 U.S.C. 154(b) by 37 days.

(21) Appl. No.: 10/498,777

(22) PCT Filed: Dec. 11, 2002

(86) PCT No.: PCT/IT02/00779

§ 371 (c)(1),
(2), (4) Date: Jun. 15, 2004

(87) PCT Pub. No.: WO03/051436

PCT Pub. Date: Jun. 26, 2003

(65) Prior Publication Data

US 2005/0096604 A1    May 5, 2005

(30) Foreign Application Priority Data

Dec. 18, 2001    (IT)    .................... MI2001A2681

(51) Int. Cl.
*A61M 5/00*    (2006.01)
(52) U.S. Cl. ...................... 604/110; 604/195
(58) Field of Classification Search ............... 604/110, 604/187, 194, 195, 218, 240
See application file for complete search history.

(56) References Cited

U.S. PATENT DOCUMENTS

| 5,378,240 | A | * | 1/1995 | Curie et al. ................. 604/110 |
| 5,389,076 | A | * | 2/1995 | Shaw .......................... 604/110 |
| 5,395,337 | A | * | 3/1995 | Clemens et al. ............. 604/110 |
| 5,395,346 | A | * | 3/1995 | Maggioni .................... 604/195 |
| 6,017,325 | A | | 1/2000 | Yerfino et al. |
| 6,632,198 | B2 | * | 10/2003 | Caizza ......................... 604/110 |
| 2004/0147876 | A1 | * | 7/2004 | Maggioni .................... 604/110 |

FOREIGN PATENT DOCUMENTS

| EP | 0 505 330 | 9/1992 |
| JP | 11-342200 | 12/1999 |

* cited by examiner

*Primary Examiner*—Kevin C. Sirmons
*Assistant Examiner*—Catherine N. Witczak
(74) *Attorney, Agent, or Firm*—Hedman & Costigan PC; James V. Costigan

(57) ABSTRACT

The present invention relates to a disposable safety syringe (1) including an automatically retractable needle (12) for preventing said syringe from being reused, comprising a cylindric body (82) defining, at one end thereof, a needle coupling end-piece (7) and being opened at the other end portion thereof for introducing thereinto a piston (4) having a scaling gasket (5). The feature of the invention is that on said piston are provided engaging means (23, 24) for engaging and retracting the needle (12) after the delivering of the injection liquid.

3 Claims, 4 Drawing Sheets

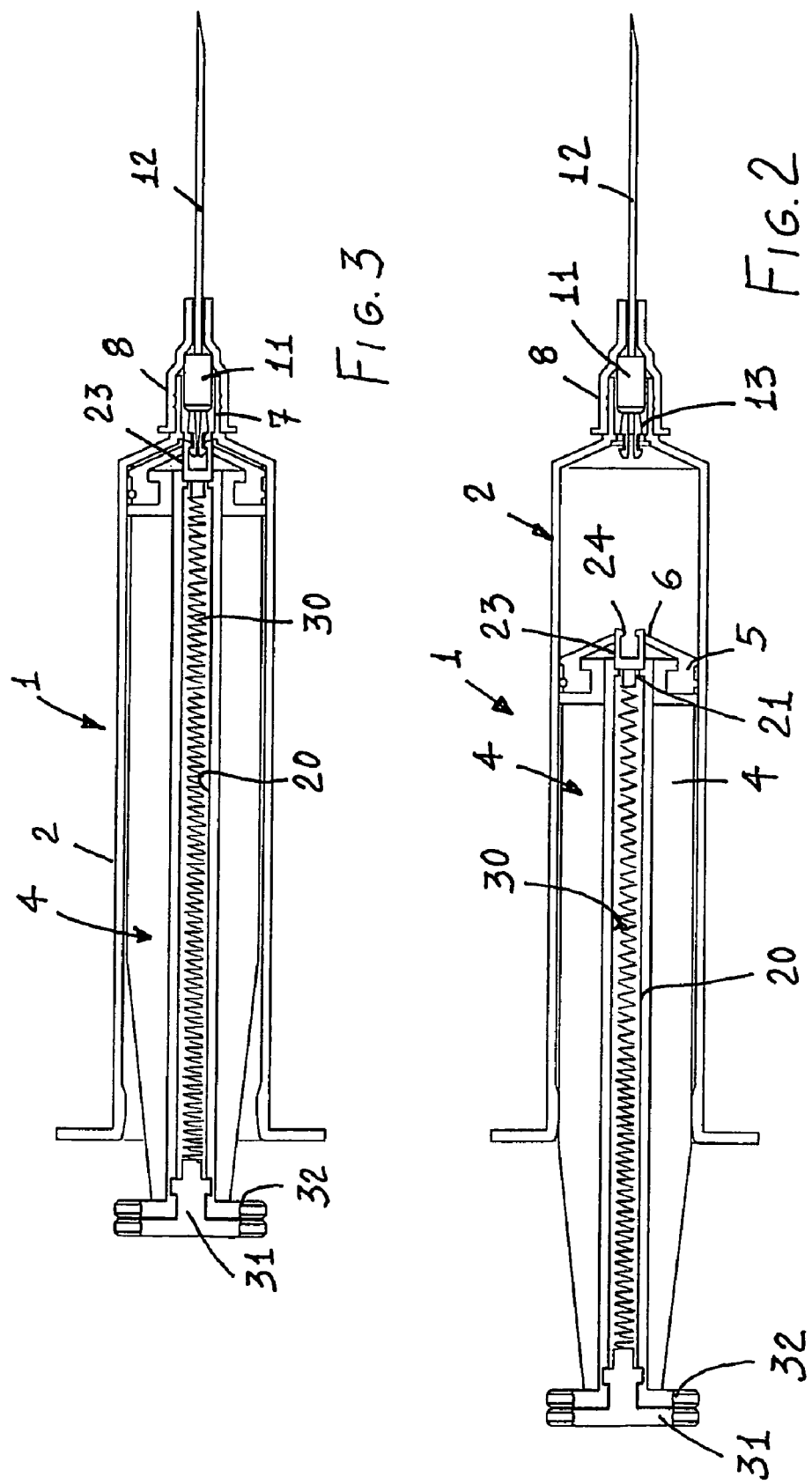

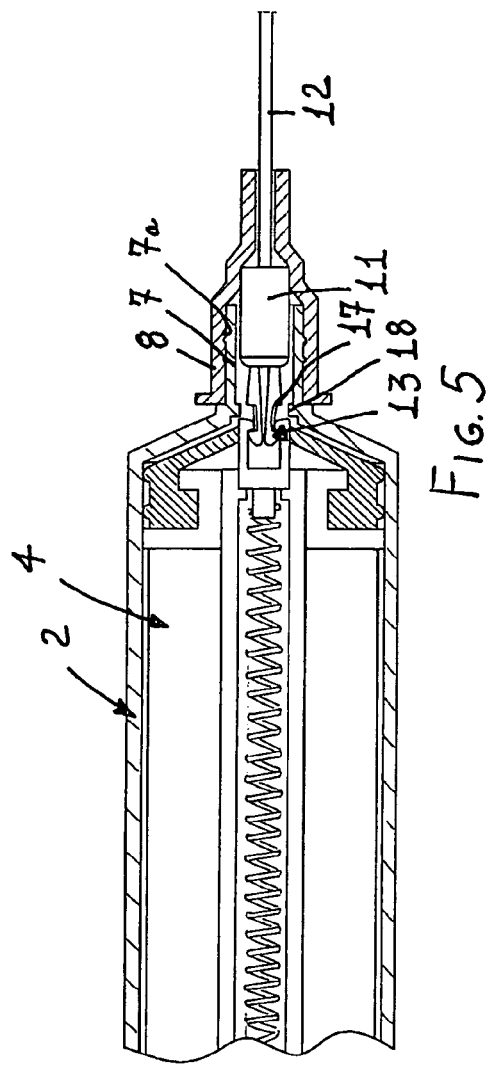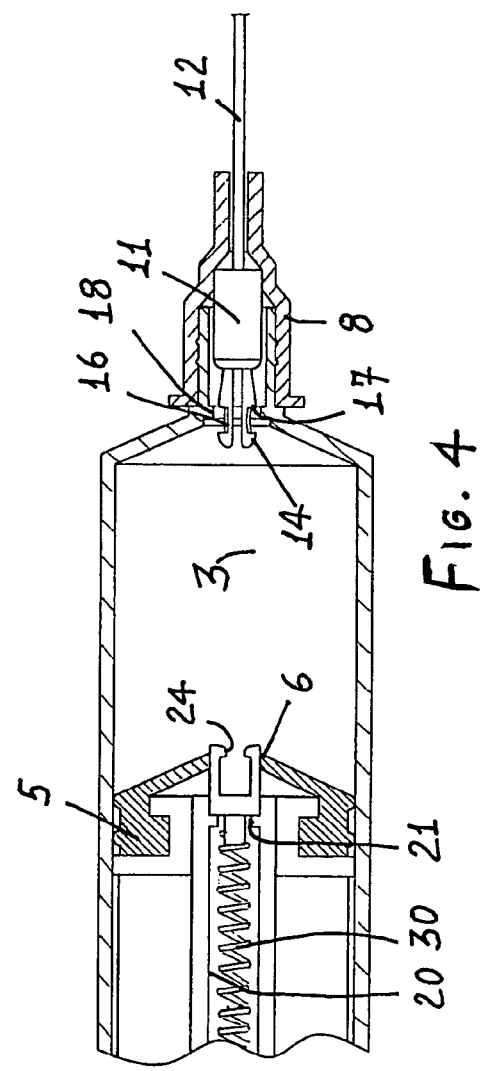

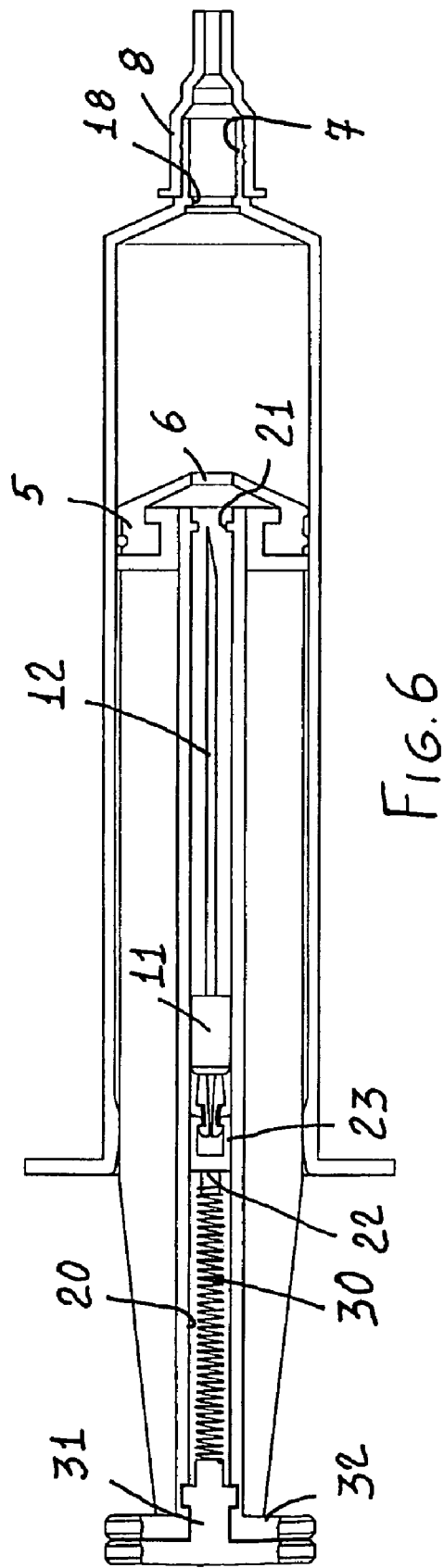

though not exclusive, embodiment of a disposable safety syringe includ-
DISPOSABLE SAFETY SYRINGE INCLUDING AN AUTOMATICALLY RETRACTABLE NEEDLE This application is a continuation of International Patent Application No. PCT/IT02/00779 filed on Dec. 11, 2002, which claims priority to Italian Application No. MI01A002681 filed on Dec. 18, 2001.

BACKGROUND OF THE INVENTION

The present invention relates to a disposable safety syringe, including an automatically retractable needle, for preventing the syringe from being reused.

As is known, a main problem of disposable syringes is that deriving from a possibility of reusing said syringes and a possibility that the syringe needle can accidentally prick the operator of the syringe.

For solving the above mentioned problem, safety syringes have been already constructed, in which are provided resilient means, operating between the syringe body and plunger, so as to cause the syringe needle to be automatically retracted, after having being used, since the syringe plunger is resiliently withdrawn from the syringe body.

Such a solution however, has not been found as practical, since, during a regular use of the syringe, it is necessary to overcome the resilient urging force provided by the spring, and which must be of a comparatively high value, in order to assure a satisfactory withdrawing of the needle but which actually hinders a proper use by the operator.

SUMMARY OF THE INVENTION

Accordingly, the aim of the present invention is to overcome the above mentioned drawbacks, by providing a disposable safety syringe, including an automatically retractable needle, for preventing the syringe from being reused, and allowing the syringe needle to be automatically retracted into the syringe body by resilient means which are inoperative during a regular use of the syringe.

Within the scope of the above mentioned aim, a main object of the present invention is to provide such a disposable safety syringe the needle of which can be retracted by very simple and efficient retracting means.

Another object of the present invention is to provide such a disposable safety syringe which, owing to its specifically designed constructional features, is very reliable and safe in operation.

Yet another object of the present invention is to provide such a disposable safety syringe which can be easily made starting from easily available elements and materials and which, moreover, is very competitive from a mere economic standpoint.

According to one aspect of the present invention, the above mentioned aim and objects, as well as yet other objects, which will become more apparent hereinafter, are achieved by a disposable safety syringe including an automatically retractable needle, said syringe comprising a syringe cylindric body defining, at one end portion thereof, an end piece for coupling the syringe needle and being opened, at the other end portion thereof, for receiving a syringe plunger including a sealing gasket, characterized in that said syringe further comprises, on said syringe plunger, engaging means for engaging and retracting said needle, after having delivered the injection liquid.

BRIEF DESCRIPTION OF THE DRAWINGS

Further characteristics and advantages of the present invention will become more apparent hereinafter from the following detailed disclosure of a preferred, though not exclusive, embodiment of a disposable safety syringe including an automatically retractable needle for preventing the syringe from being reused, and being illustrated, by way of an indicative but not limitative example, in the accompanying drawings, where:

FIG. 2 is a cross-sectional view of the syringe illustrating said syringe in a use condition thereof;

FIG. 3 is a schematic view illustrating the end step of the injectable liquid delivering operation;

FIG. 4 illustrates, on an enlarged scale, the position assumed by the needle and plunger of FIG. 2;

FIG. 5 illustrates, on an enlarged scale, the position of the syringe needle and plunger or piston in the condition shown in FIG. 3; and FIG. 6 is a schematic view illustrating the retracting operation for retracting the syringe needle being performed by resilient means.

DESCRIPTION OF THE PREFERRED EMBODIMENTS

Figure 1:
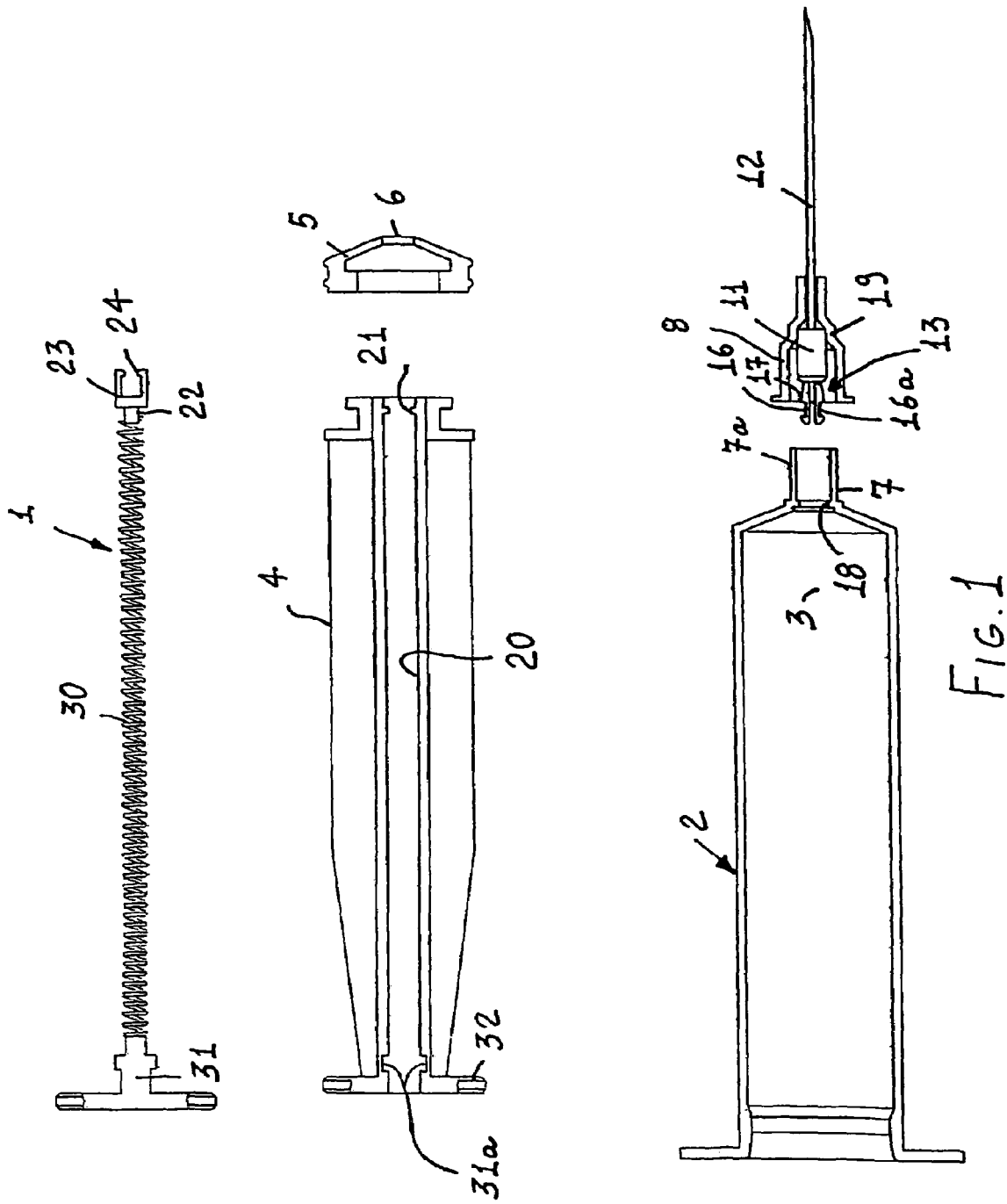
FIG. 1 is a schematic exploded view illustrating the disposable safety syringe according to the present invention.

With reference to the number references of the above mentioned figures, the disposable safety syringe, including a retractable needle, according to the present invention, which has been generally indicated by the reference number 1, comprises a syringe cylindric body 2, defining an inner chamber 3, in which a syringe piston or plunger can slide, said syringe plunger or piston being indicated by the reference number 4 and including a sealing front gasket 5 having a central opening 6, as it will become more apparent hereinafter.

Making now reference to the syringe constructional details, the syringe cylindric body 2 is provided, at one end portion thereof, with an end piece 7, thereon is applied a cap 8, housing in its inside a barrel element 11 which, at one end thereof, is coupled to a syringe needle 12 and, at the other end thereof, comprises resiliently spreadable wings, generally indicated by the reference number 13.

Said wings comprise a tapering portion 14 at their free end, adjoining cut-outs 16 ending with a tooth element 17, abutting against an abutment ring element 18 provided in the attachment region of the end-piece 7.

On the outer surface of the end-piece 7 are provided a plurality of slots 7a for improving the engagement of the cap 8.

Moreover, a further cut-out 16a is provided, which has a curved configuration, so as to substantially prevent the syringe needle from being re-engaged in the mentioned cap as it is withdrawn.

As shown, the cap 8 comprises a cylindric surface 19, therein said barrel element 11 is engaged for providing the required sealing.

The syringe plunger 4 defines, according to a feature of the invention, an axial cavity 20 which, at its portions thereat said gasket 5 is arranged, comprises a stop abutment 21 engaging, as the syringe is used, with an abutment element 22 defined by a nose 23 having clamping elements 24 which can be engaged with the mentioned resilient wings, as it will become more apparent hereinafter.

The nose 23 is coupled to recovering resilient means or spring 30, housed in said axial cavity 20 and which, at the other end portion thereof, engages with a pawl 31, which can be locked in a corresponding depression 31a at the flanged bottom portion 32 of the syringe plunger 4.

With the disclosed arrangement, the nose 23 projects from said central hole or opening 6 and is restrained in a stop abutment position by the stop abutment 21 engaging with the abutment 22.

As the syringe is used, and as shown in FIGS. 2 and 4, the syringe plunger will perform its operating stroke to inject the injection liquid.

Under such a condition, the syringe needle is firmly held in its position due to the provision of the cap 8 and because of the engagement of the engagement of the tooth elements 17 with the locking abutment 18.

At the end of the injection, the clamping elements 24 of the nose 23, by engaging with the tapering portions 14, will cause the wings 13 to be radially contracted, thereby disengaging the tooth elements 17 from the abutment 18, so as to allow the syringe needle to be disengaged from the mentioned cap.

Moreover, the nose 23 can disengage from the stop abutments 21, under a pushing force, and owing to the provision of the return spring 30, causing the needle to be immediately retracted, inside the axial cavity 20, as is clearly shown in FIG. 6.

In such a condition, the syringe cannot be absolutely reused.

Moreover, the needle will be arranged at a protected region thereby preventing any inuring to the syringe operator.

From the above disclosure it should be apparent that the invention fully achieves the intended aim and objects.

In particular, it is pointed out that a safety disposable syringe has been provided which, while having a very simple construction, allows the syringe needle to be automatically retracted upon the injection.

The invention, as disclosed, is susceptible to several modifications and variations, all of which will come within the scope of the invention.

Moreover, all of the constructional details can be replaced by other technically equivalent elements, depending on requirements.

The invention claimed is:

1. A disposable safety syringe including an automatically retractable needle, said syringe comprising a cylindrical syringe body defining, at a top end portion thereof, a top end piece for coupling a syringe needle, said cylindrical syringe body being opened at a bottom end portion thereof, for receiving a syringe plunger including a top sealing gasket having a central opening, and an inner axial cylindrical cavity extending substantially through the overall length of said plunger, said syringe needle being coupled to a cylindrical barrel element including two bottom resilient wings having cut-outs delimited by an abutment tooth element to prevent said needle from being retracted, said syringe further comprising, in said axial cavity, needle engaging and tetracting means for engaging said needle into said axial cavity and retracting said needle out of said axial cavity, said engaging and retracting means comprising a fork nose slidably engaged in said axial cavity and adapted to engage said resilient wings to withdraw said syringe needle into said axial cavity, said fork nose being arranged at a top portion of a needle withdrawing spring arranged in said axial cavity, at least one of said cut-outs defined on said resilient wings being curved so as to cause said needle to be fully withdrawn in said axial cavity with a slightly slanted orientation to prevent said needle from exiting again, that said axial cavity defines, at a top portion thereof, two inward directed opposite stop abutments against which said cylindrical barrel element abuts, said spring being engaged, at a bottom portion thereof, with a pawl including two top horizontally projecting portions engageable in corresponding depressions formed in a flanged bottom portion of said axial cavity, said top end piece of said cylindrical syringe body being covered by a cap, said cap also tightly covering said cylindrical barrel element.

2. A disposable safety syringe, according to claim 1, wherein said nose has a size adapted to pass through said central opening of said plunger gasket, said spring being resiliently preloaded for retracting said needle at the end of an injection liquid delivery operation.

3. A disposable safety syringe, according to claim 1, wherein said top end piece of said cylindrical syringe body has a grooved outer surface.

* * * * *